(12) United States Patent
Taniike et al.

(10) Patent No.: US 7,022,218 B2
(45) Date of Patent: Apr. 4, 2006

(54) BIOSENSOR WITH INTERDIGITATED ELECTRODES

(75) Inventors: Yuko Taniike, Osaka (JP); Shin Ikeda, Katano (JP); Toshihiko Yoshioka, Hirakata (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 35 days.

(21) Appl. No.: 10/333,232

(22) PCT Filed: May 27, 2002

(86) PCT No.: PCT/JP02/05129

§ 371 (c)(1),
(2), (4) Date: Jan. 15, 2003

(87) PCT Pub. No.: WO02/097418

PCT Pub. Date: Dec. 5, 2002

(65) Prior Publication Data

US 2004/0005721 A1    Jan. 8, 2004

(30) Foreign Application Priority Data

May 29, 2001    (JP)    ............................. 2001-161244

(51) Int. Cl.
*G01N 27/327*    (2006.01)
*G01N 27/26*    (2006.01)

(52) U.S. Cl. ............................. 205/777.5; 204/403.01; 204/403.02; 204/403.04; 204/403.14

(58) Field of Classification Search .................. 204/403.01–403.15; 205/777.5
See application file for complete search history.

(56) References Cited

U.S. PATENT DOCUMENTS

| 5,001,048 A | * | 3/1991 | Taylor et al. .................. 435/4 |
| 5,670,031 A | | 9/1997 | Hintsche et al. |
| 6,592,745 B1 | | 7/2003 | Feldman et al. |

FOREIGN PATENT DOCUMENTS

EP    0 984 069 A2    3/2000

(Continued)

*Primary Examiner*—Nam Nguyen
*Assistant Examiner*—Jeffrey T. Barton
(74) *Attorney, Agent, or Firm*—Akin Gump Strauss Hauer & Feld, LLP

(57) ABSTRACT

The present invention provides a highly sensitive biosensor capable of yielding good response even when the amount of a sample is extremely small. The biosensor of the present invention includes: a first insulating base plate which has a working electrode comprising a plurality of branches and a first counter electrode comprising a plurality of branches, the branches of the working electrode and the first counter electrode being arranged alternately; a second insulating base plate which has a second counter electrode and which is disposed at a position opposite to the first insulating base plate; a reagent system comprising an oxidoreductase; and a sample supply pathway formed between the first and second insulating base plates, wherein the branches of the working electrode and the first counter electrode that are arranged alternately, the second counter electrode, and the reagent system are exposed in the sample supply pathway.

4 Claims, 7 Drawing Sheets

FOREIGN PATENT DOCUMENTS

| | | |
|---|---|---|
| JP | 01-272958 A | 10/1989 |
| JP | 03-202764 A | 9/1991 |
| JP | 07-260737 A | 10/1995 |
| JP | 09-159644 A | 6/1997 |
| JP | 09-243590 A | 9/1997 |
| JP | 11-064271 A | 3/1999 |
| JP | 2000065777 | 3/2000 |
| JP | 2000065778 A * | 3/2000 |
| JP | 2000-121593 A | 4/2000 |
| WO | 00/62047 A1 | 10/2000 |

* cited by examiner

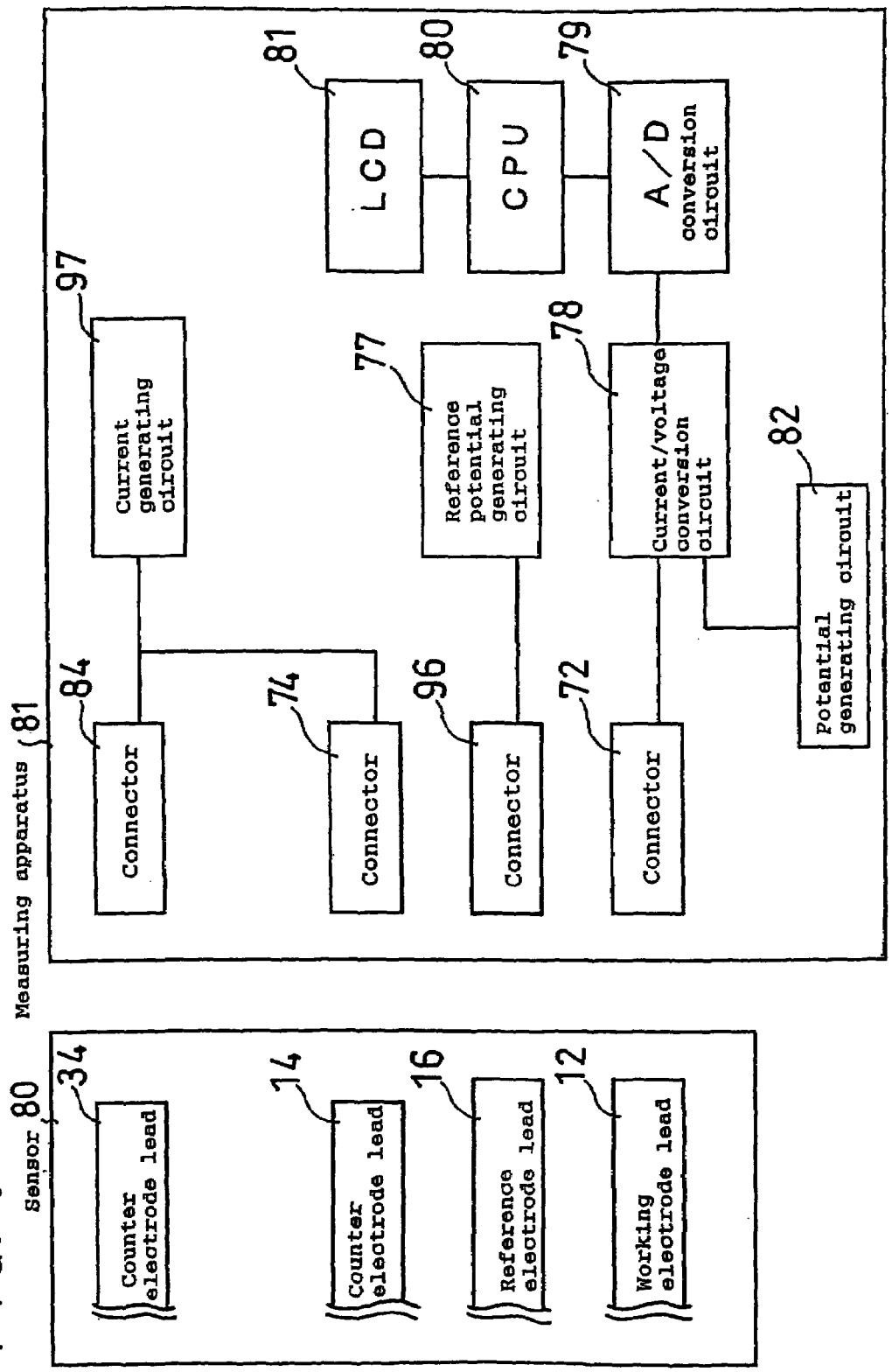

US 7,022,218 B2

BIOSENSOR WITH INTERDIGITATED ELECTRODES

CROSS-REFERENCE TO RELATED APPLICATION

This application is the national phase under 35 U.S.C. §371 of PCT International Application No. PCT/JP02/05129, which has an international filing date of May 27, 2002, and which designated the United States of America.

TECHNICAL FIELD

The present invention relates to a biosensor for rapid and highly accurate quantification of a substrate contained in a sample.

BACKGROUND ART

Methods using polarimetry, colorimetry, reductimetry and a variety of chromatographies have been developed as methods for quantitative analysis of sugars such as sucrose and glucose. These methods, however, are all poorly specific to sugars and hence have poor accuracy. Among these methods, the polarimetry is simple in manipulation, but is largely affected by the temperature during the manipulation. Therefore, the polarimetry is not suitable as a method of simple quantification of sugars at home, etc. for ordinary people.

Recently, various types of biosensors utilizing the specific catalytic action of enzymes have been under development.

The following will describe a method of glucose quantification as one example of the method of quantifying a substrate contained in a sample. As an electrochemical method of glucose quantification, a method using glucose oxidase (EC 1.1.3.4: hereinafter abbreviated to GOD) as an enzyme and an oxygen electrode or a hydrogen peroxide electrode is generally well-known (see "Biosensor" ed. by Shuichi Suzuki, Kodansha, for example).

GOD selectively oxidizes β-D-glucose as a substrate to D-glucono-δ-lactone using oxygen as an electron mediator. In the oxidation reaction process by GOD in the presence of oxygen, oxygen is reduced to hydrogen peroxide. The decreased amount of oxygen is measured by the oxygen electrode, or the increased amount of hydrogen peroxide is measured by the hydrogen peroxide electrode. Since the decreased amount of oxygen and the increased amount of hydrogen peroxide are proportional to the content of glucose in the sample, glucose quantification is possible based on the decreased amount of oxygen or the increased amount of hydrogen peroxide.

The above method utilizes the specificity of enzyme reactions to enable accurate quantification of glucose in the sample. However, as speculated from the reaction process, it has a drawback in that the measurement is largely affected by the oxygen concentration of the sample, and if the oxygen is absent in the sample, the measurement is infeasible.

Under such circumstances, glucose sensors of new type have been developed which use as the electron mediator potassium ferricyanide, an organic compound or a metal complex such as a ferrocene derivative and a quinone derivative without using oxygen as the electron mediator. In the sensors of this type, the reduced form of the electron mediator which results from the enzyme reaction is oxidized on a working electrode, and based on the amount of this oxidation current, the concentration of glucose contained in the sample can be determined. Simultaneously, on a counter electrode, a reaction in which the oxidized form of the electron mediator is reduced into the reduced form of the electron mediator proceeds. With the use of such an organic compound or metal complex as the electron mediator in place of oxygen, it is possible to form a reagent layer comprising a known amount of GOD and the electron mediator which are carried in a stable state and a precise manner on the electrodes, so that accurate quantification of glucose is possible without being affected by the oxygen concentration of the sample. In this case, it is also possible to integrate the reagent layer containing the enzyme and electron mediator, in an almost dry state, with an electrode system, and hence disposable glucose sensors based on this technique have recently been receiving a lot of attention. A typical example thereof is a biosensor disclosed in Japanese Patent Publication No. 2517153. With such a disposable glucose sensor, by simply introducing a sample into the sensor connected detachably to a measurement device, glucose concentration can be measured readily by the measurement device.

According to the measurement method using the above-described glucose sensor, with the use of a sample whose amount is in the order of several μl, the concentration of a substrate in the sample can be determined readily. However, in recent years, it is anxiously desired in various fields to develop biosensors capable of measuring a sample in an extremely small amount of not more than 1 μl. When a sample in an extremely small amount is measured by a conventional electrochemical glucose sensor, the amount of glucose in the sample is also extremely small, and hence the sensitivity of the measurement may lower in some cases.

Thus, there has been developed a biosensor which utilizes two substantially comb-shaped electrodes comprising a plurality of branches that are arranged alternately on a base plate. FIG. 7 is a sectional view of the biosensor in the vicinity of the electrode system. In this type of sensor, the oxidized form of an electron mediator, which results from the oxidation at a first electrode 1 disposed on a base plate 5, can be reduced back to the reduced form at a neighboring second electrode 3, and the reduced form can be oxidized again at a neighboring first electrode 1. Accordingly, the value of the current flowing through the first electrode 1 increases apparently, so that more sensitive glucose quantification is possible in comparison with conventional biosensors.

This approach is applicable not only to glucose quantification but also to quantification of other substrates contained in a sample.

However, since there has been a demand in recent years for further reduction in the amount of a sample necessary for making a measurement, glucose sensors having higher sensitivity are anxiously desired in various fields.

In view of the above, an object of the present invention is to provide a highly sensitive biosensor capable of giving good response even when the amount of a sample is extremely small.

DISCLOSURE OF INVENTION

A biosensor of the present invention includes: a first insulating base plate which has a working electrode comprising a plurality of branches and a first counter electrode comprising a plurality of branches, the branches of the working electrode and the first counter electrode being arranged alternately; a second insulating base plate which has a second counter electrode and which is disposed at a position opposite to the first insulating base plate; a reagent system comprising an oxidoreductase; and a sample supply pathway formed between the first and second insulating base plates, wherein the branches of the working electrode and the first counter electrode that are arranged alternately, the second counter electrode, and the reagent system are exposed in the sample supply pathway.

It is preferred that the second counter electrode be disposed only at a position opposite to the working electrode in the sample supply pathway.

The present invention provides a biosensor including: a first insulating base plate which has a first working electrode comprising a plurality of branches and a first counter electrode comprising a plurality of branches, the branches of the first working electrode and the first counter electrode being arranged alternately; a second insulating base plate which has a second working electrode comprising a plurality of branches and a second counter electrode comprising a plurality of branches, the branches of the second working electrode and the second counter electrode being arranged alternately; a reagent system comprising an oxidoreductase; and a sample supply pathway formed between the first and second insulating base plates, wherein the branches of the first working electrode and the first counter electrode that are arranged alternately, the branches of the second working electrode and the second counter electrode that are arranged alternately, and the reagent system are exposed in the sample supply pathway.

It is preferred that the second counter electrode be disposed at a position opposite to the first working electrode and that the second working electrode be disposed at a position opposite to the first counter electrode.

BRIEF DESCRIPTION OF DRAWINGS

FIG. 9 is a block diagram showing the circuit structure of a measuring apparatus to which a sensor in another embodiment of the present invention is set.

BEST MODE FOR CARRYING OUT THE INVENTION

In the following, embodiments of the biosensor of the present invention will be described with reference to drawings.

The shape and structure of for example the first base plate and the second plate and the shape, material and branch number of the electrodes are not to be limited to the embodiments as described below.

Embodiment 1

Figure 1:
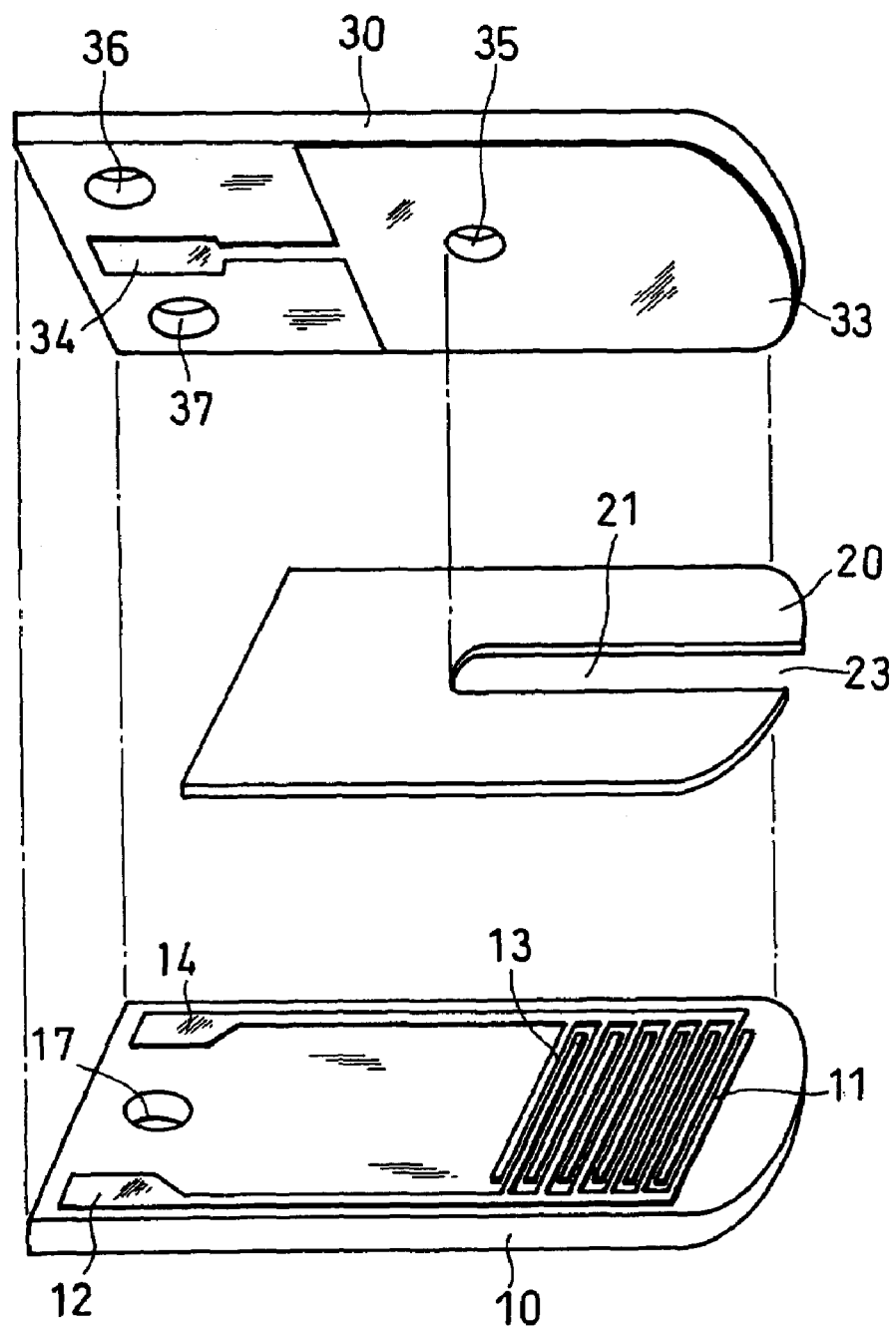
FIG. 1 is an exploded perspective view of a glucose sensor from which the reagent layer is omitted in one embodiment of the present invention.

FIG. 1 is a longitudinal cross-sectional view of a glucose sensor from which the reagent layer and surfactant layer are omitted in this embodiment.

10 represents a first base plate comprising an electrically insulating material. On the base plate 10, there is formed, by photo lithography, an electrode system which is composed of a substantially comb-shaped working electrode 11 comprising a plurality of branches and its lead 12 and a substantially comb-shaped first counter electrode 13 comprising a plurality of branches and its lead 14. As a specific method, for example, palladium is sputtered over the base plate, and the palladium film is covered with a resist. Subsequently, the resultant palladium film is provided with masking having the same shape as the electrode system, exposed to light, developed, and etched. Finally, the resist is removed to form an electrode system having a predetermined shape. In this figure, each of the working electrode 11 and the first counter electrode is illustrated as having six branches, but there is no limitation thereto. As described in the examples given below, it may be composed of dozens of branches. Over a second base plate 30 comprising an electrically insulating material, palladium is sputtered, to form a second counter electrode 33 and its lead 34. The second base plate 30 has an air vent 35. The first base plate 10 is provided with an electrically connecting hole 17 for bringing a terminal of an apparatus in contact with the second counter electrode lead 34, and the second base plate 30 is provided with electrically connecting holes 36 and 37 for bringing terminals of the apparatus in contact with the working electrode lead 12 and the lead 14 of the first counter electrode 13.

A spacer member 20 comprising an insulating material has a slit 21 for forming a sample supply pathway that will be described below. After the spacer member 20 is bonded to the first base plate 10, a reagent layer is formed by dropping a solution for forming a reagent layer from the slit 21 on the electrode system and drying it. The reagent layer contains GOD, which is an oxidoreductase, and potassium ferricyanide, which is an electron mediator. It is preferable to form a surfactant layer comprising lecithin as a surfactant on the reagent layer.

Next, the second base plate 30 is bonded to the first base plate 10 that is joined with the spacer 20 in a positional relation as indicated by the dash-dotted lines of FIG. 1, to fabricate a glucose sensor. Then, between the first base plate and the second base plate in the slit 21 of the spacer 20 is formed a sample supply pathway. An open end 23 of the slit 21 serves as a sample supply inlet, and the air vent 35 of the second base plate 30 is the end of the sample supply pathway.

In the sample supply pathway, the electrode system and the second counter electrode are disposed so as to face each other. And, the spacer 20 defines the area of the working electrode 11, first counter electrode 13 and second counter electrode 33 facing the sample supply pathway (electrode area).

Figure 8:
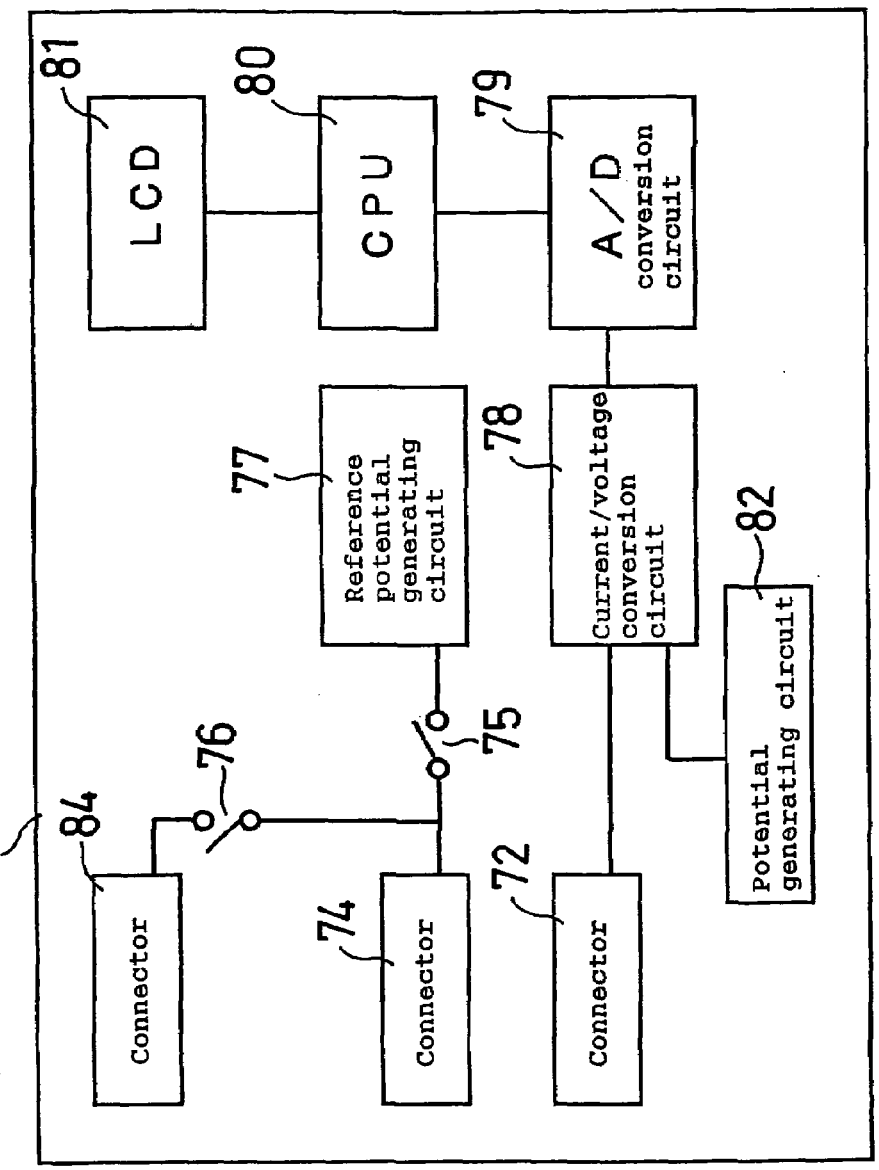
FIG. 8 is a block diagram showing the circuit structure of a measuring apparatus to which a sensor in one embodiment of the present invention is set.

In the following, a measuring apparatus for measuring glucose with the use of this sensor will be described with reference to FIG. 8.

A sensor 70, which was described above, is shown on the left side of FIG. 8. In this figure, only the working electrode lead 12, the first counter electrode lead 14 and the second counter electrode lead 34 are shown. Meanwhile, a measuring apparatus 71 comprises connectors 72, 74 and 84 which are connected to the leads 12, 14 and 34, respectively. The connector 84 is connected to the connector 74 via a switch 76, and they are connected to a reference potential generating circuit 77 via a switch 75. To the connector 72 is connected a potential generating circuit 82 and a current/voltage conversion circuit 78. The current/voltage conversion circuit 78 converts, into voltage, the current flowing between the working electrode and the counter electrode upon application of a positive potential to the working electrode with respect to the counter electrode connected to the reference potential generating circuit 77 for output. The output voltage is converted into pulses by an A/D conversion circuit 79. A CPU 80 calculates the amount of a substrate contained in a sample based on the pulses output from the A/D conversion circuit 79. The calculated value is displayed on an LCD 81.

The sensor 70 is set to the above-described measuring apparatus 71, and the switch 76 of the measuring apparatus is closed to short-circuit the first counter electrode 13 and the second counter electrode 33 while the switch 75 is closed. When a sample containing glucose is brought in contact with the sample supply inlet 23 at the end of the sensor, the sample readily reaches the reagent layer in the sample supply pathway by capillarity. Upon the detection of arrival of the sample at the electrode system, the measuring apparatus starts operating and a timer starts measuring time. When the reagent layer is dissolved by the sample, glucose is oxidized by GOD while the electron mediator potassium ferricyanide is reduced to potassium ferrocyanide. After a lapse of an appropriate time from the start of operation of the apparatus, a voltage of 300 mV is applied to the working electrode 11 with respect to the counter electrode from the potential generating circuit 82, and a current oxidizing the potassium ferrocyanide flows between the working electrode 11 and the counter electrode. By the functions of the current/voltage conversion circuit 78 and other components of the measuring apparatus, the glucose concentration based on this current value is displayed on the LCD 81.

Figure 2:
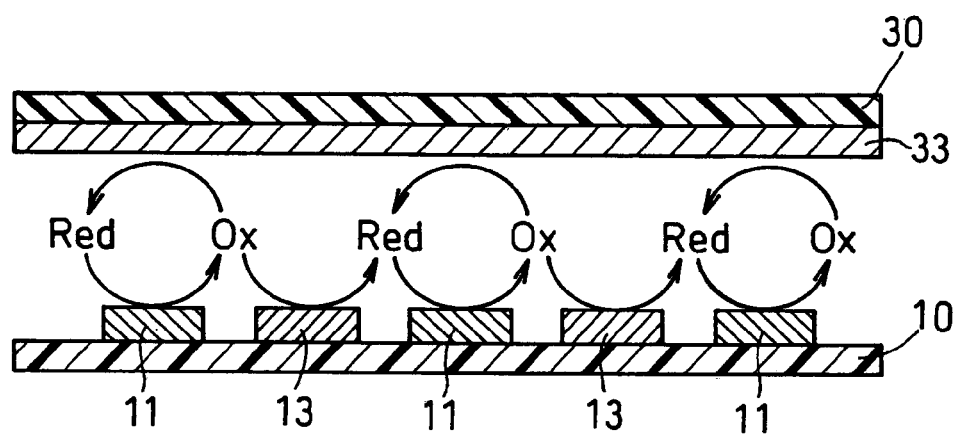
FIG. 2 is a cross sectional view showing the arrangement of electrodes in a sample supply pathway of the same sensor.

FIG. 2 illustrates the flow of the current oxidizing the electron mediator in the vicinity of the electrode system of the biosensor in this embodiment. In this embodiment, the working electrode 11 and the first counter electrode 13 have a plurality of branches, and these branches are alternately arranged to form the electrode system. The second counter electrode 33 is disposed so as to oppose this electrode system. With this structure, the oxidized form electron mediator which results from the oxidation at the working electrode 11 disposed on the first base plate 10 is reduced at the adjoining first counter electrode 13, while the oxidized form electron mediator which has diffused in a direction perpendicular to the working electrode 11 is also reduced back to the reduced form on the second counter electrode 33 disposed on the second base plate 30. Further, due to the suppression of the growth of the diffusion layer on the working electrode 11, the concentration of the oxidation/reduction species on the second counter electrode 33 is reflected in the sensor response. For these reasons, the sensor response of the biosensor of this embodiment increases in comparison with conventional biosensors.

Figure 3:
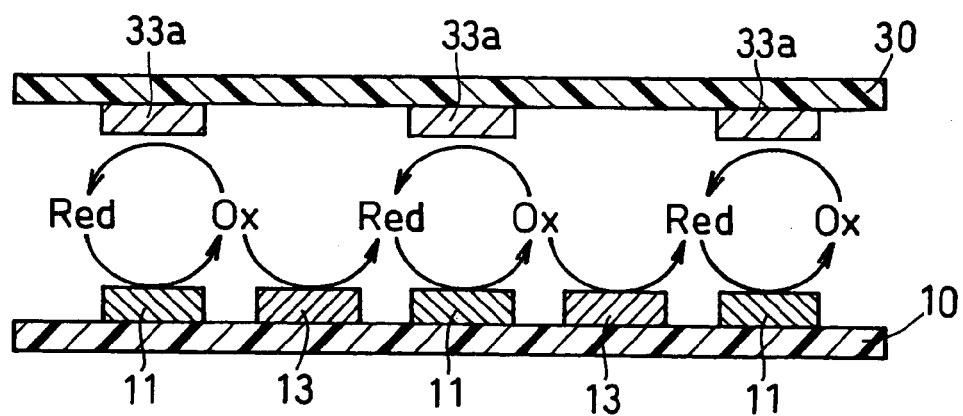
FIG. 3 is a cross sectional view showing another example of the arrangement of electrodes in a sample supply pathway of a sensor.

Therein, it is preferred that the second counter electrode is disposed only at a position opposite to the working electrode. That is, as illustrated in FIG. 3, the second counter electrode 33 is trimmed into a comb shape having a plurality of branches 33a. The second counter electrode has a structure in which their branches 33a are opposed to the branches of the working electrode in the sample supply pathway. With this structure, the concentration of the reduced form electron mediator in the vicinity of the second counter electrode is heightened, probably because the current density in the vicinity of the second counter electrode immediately above the working electrode is heightened, or for other reasons. Since the sensor response depends on the concentration of the reduced form electron mediator, highly sensitive quantification of the substrate consequently becomes possible.

Embodiment 2

Figure 4:
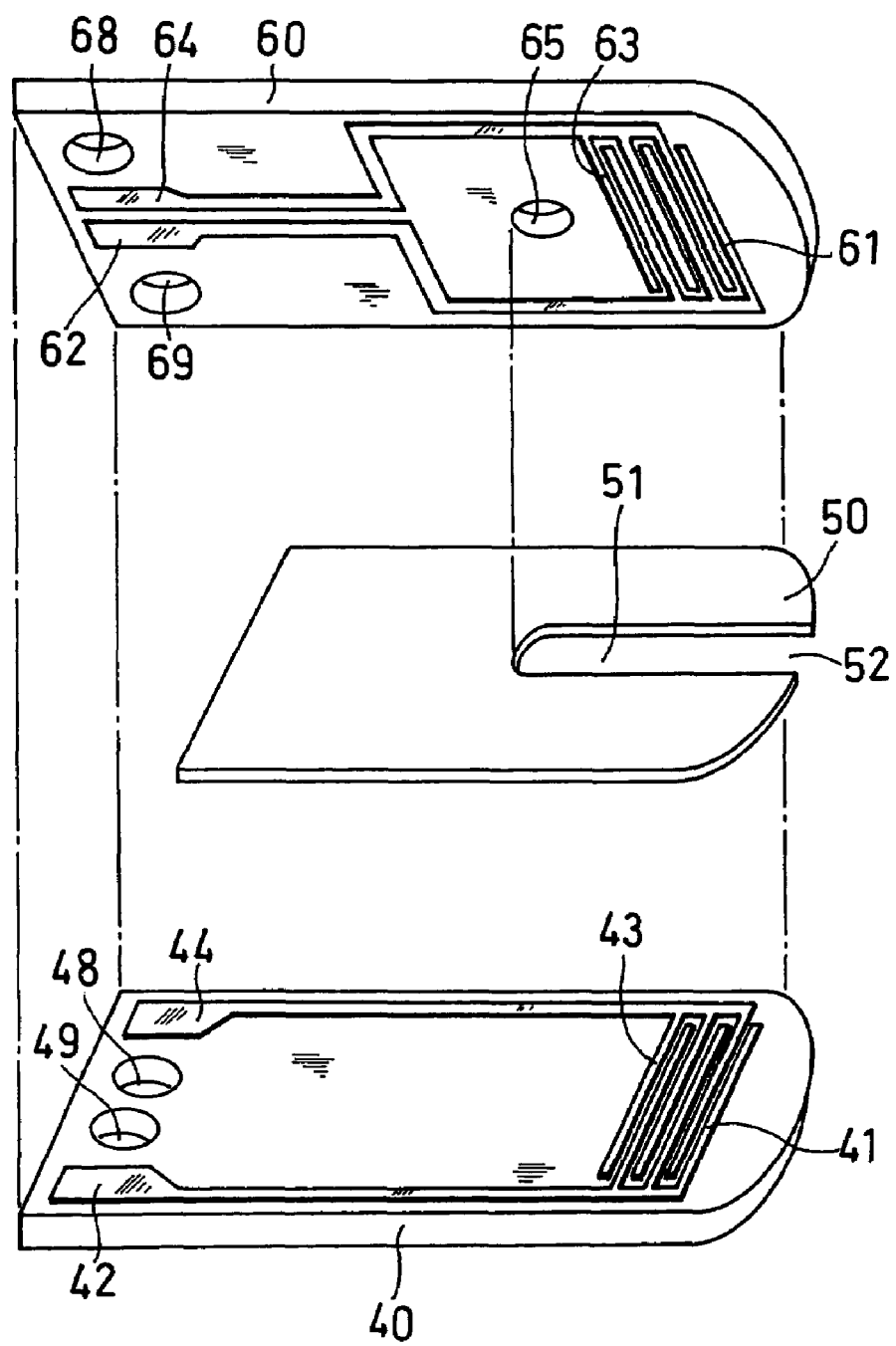
FIG. 4 is an exploded perspective view of a biosensor from which the reagent layer is omitted in another embodiment of the present invention.

FIG. 4 is a decomposed perspective view of a glucose sensor from which the reagent layer and surfactant layer are omitted in this embodiment.

Following the same procedure as that of Embodiment 1, a first electrode system, which is composed of a substantially comb-shaped first working electrode 41 comprising a plurality of branches, a first working electrode lead 42, a substantially comb-shaped first counter electrode 43 comprising a plurality of branches and a first counter electrode lead 44, is formed on a first base plate 40. On a second base plate 60 is formed a second electrode system, which is composed of a substantially comb-shaped second working electrode 61 comprising a plurality of branches, a second working electrode lead 62, a substantially comb-shaped second counter electrode 63 comprising a plurality of branches and a second counter electrode lead 64. The number of the branches of the working electrode and the counter electrode is not to be limited to the number as illustrated in this figure in the same manner as in Embodiment 1. The second base plate 60 has an air vent 65. The first base plate 40 is provided with electrically connecting holes 48 and 49 for bringing terminals of an apparatus in contact with the second counter electrode lead 62 and the second working electrode lead 64. Likewise, the second base plate 60 is provided with electrically connecting holes 68 and 69 for bringing terminals of the apparatus in contact with the first working electrode lead 42 and the first counter electrode lead 44.

Thereafter, a spacer member 50 is bonded to the first base plate 40, a reagent layer is formed thereon, and the second base plate 60 is bonded thereto in a positional relation as indicated by the dash-dotted lines of FIG. 4, to fabricate a glucose sensor. The spacer 50 has a slit 51 for forming a sample supply pathway. An open end 52 of the slit 51 serves as a sample supply inlet.

In this way, the sample supply pathway is formed in the slit 51 of the spacer 50 between the first base plate 40 and the second base plate 60. In the sample supply pathway, as illustrated in FIG. 4, the second counter electrode 63 is disposed at a position opposite to the first working electrode 41, and the second working electrode 61 is disposed at a position opposite to the first counter electrode 43. The slit 51 of the spacer 50 defines the area of the first working electrode 41, first counter electrode 43, second working electrode 61 and second counter electrode 63 facing the sample supply pathway (electrode area). In the sensor of this embodiment, the total electrode area of the first working electrode 41 and the second working electrode 61 is made equal to the electrode area of the working electrode 11 of Embodiment 1. However, since the second working electrode 61 is disposed on the second base plate 60, the electrode system formed is denser in comparison with the sensor of Embodiment 1. Therefore, in comparison with the sensor of Embodiment 1, the size of the slit 51 can be made smaller, resulting in a reduction in the amount of the sample.

Therein, it is preferable that the second counter electrode be disposed at a position opposite to the first working electrode and that the second working electrode be disposed at a position opposite to the first counter electrode.

Figure 5:
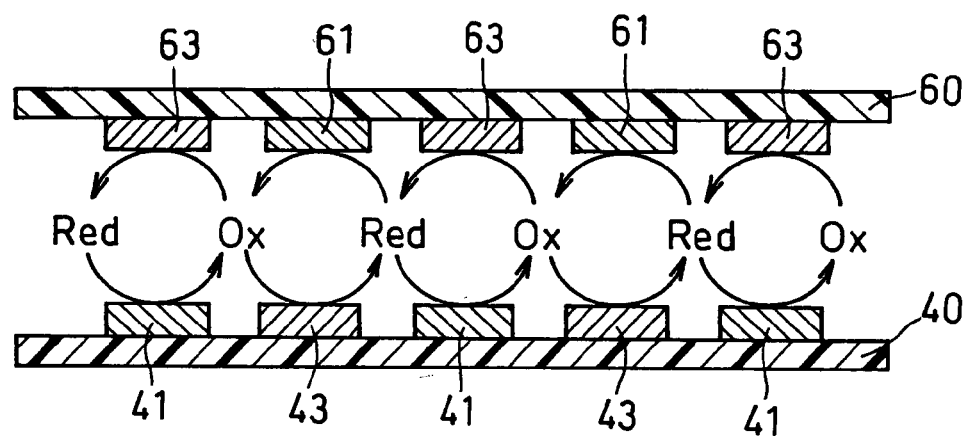
FIG. 5 is a cross sectional view showing the arrangement of electrodes in a sample supply pathway of the same sensor.
Figure 7:
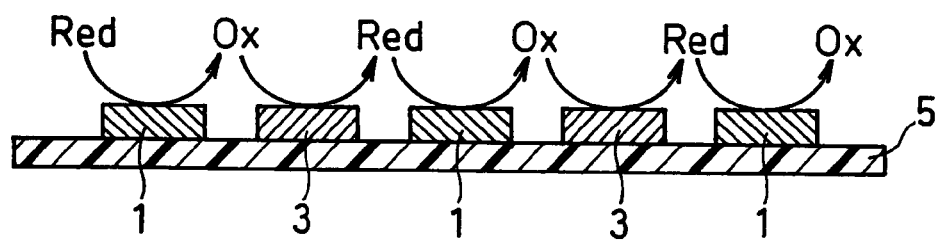
FIG. 7 is a cross sectional view showing the arrangement of electrodes of a conventional biosensor.

FIG. 5 illustrates the arrangement of the electrodes in the sample supply pathway of the biosensor in this embodiment. The first working electrode 41 and the first counter electrode 43 disposed on the first base plate 40 are alternately arranged, and the second working electrode 61 and the second counter electrode 63 disposed on the second base plate 60 are alternately arranged; the first working electrode 41 and the second counter electrode 63 are opposed to each other, and the first counter electrode 43 and the second working electrode 61 are opposed to each other. Accordingly, in comparison with the biosensor as illustrated in FIG. 2, a denser electrode system can be disposed when the total area of the working electrode is the same. Therefore, the volume of the sample supply pathway can be reduced, and hence reduction of the amount of a sample becomes possible.

Embodiment 3

Figure 6:
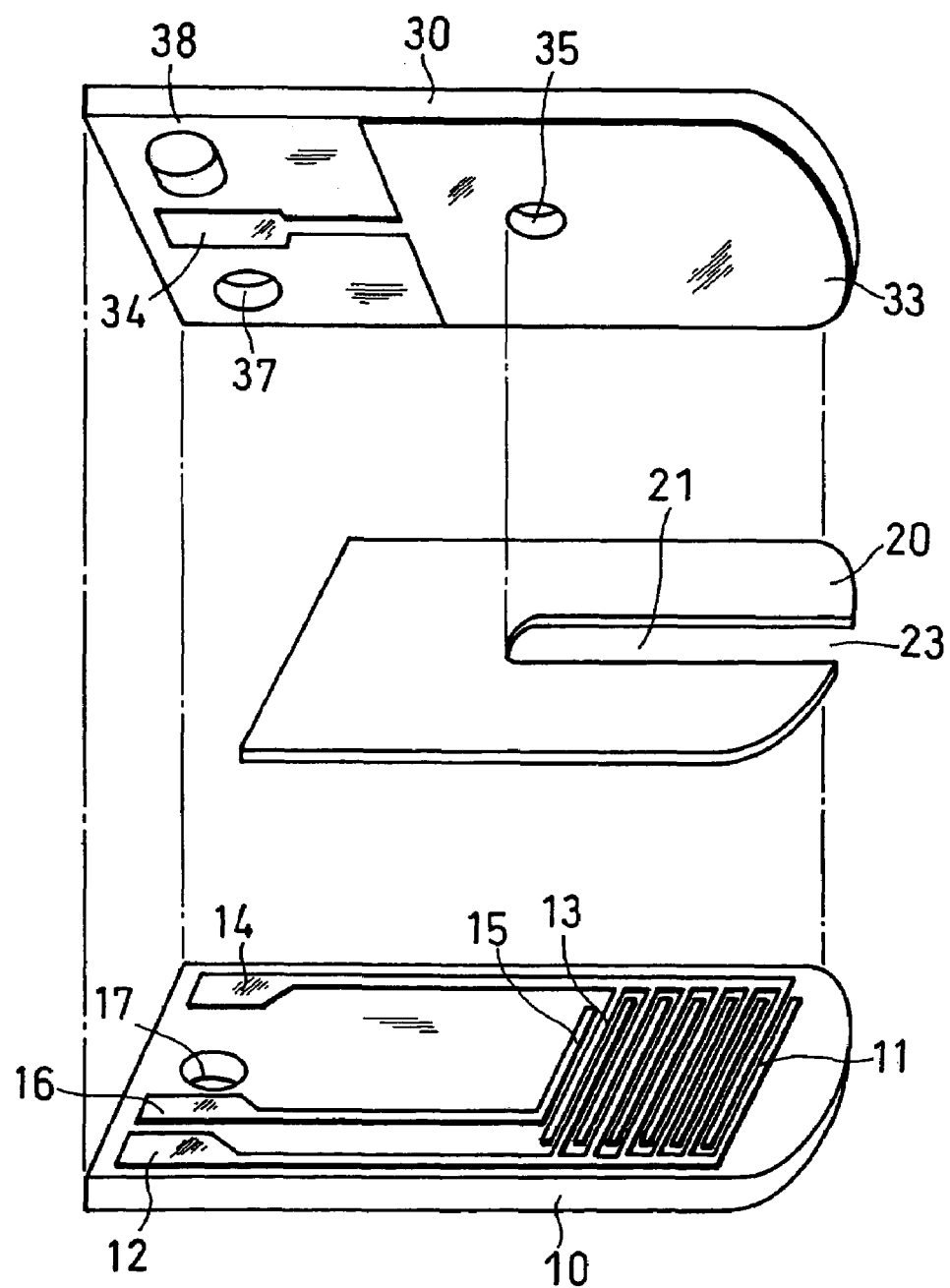
FIG. 6 is an exploded perspective view of a biosensor from which the reagent layer is omitted in still another embodiment of the present invention.

FIG. 6 is a decomposed perspective view of a glucose sensor from which the reagent layer and surfactant layer are omitted in this embodiment.

The structure is the same as that of Embodiment 1 except for the formation of a reference electrode 15 and its lead 16 on a first base plate 10 and formation of an electrically connecting hole 38 for bringing a working electrode lead 12 and the lead 16 of the reference electrode 15 in contact with two corresponding terminals of an apparatus on a second base plate 30.

In the following, a measuring apparatus for measuring glucose with the use of this sensor will be described with reference to FIG. 9.

A sensor 80, which was described above, is shown on the left side of FIG. 9. In this figure, only the working electrode lead 12, the lead 16 of the first reference electrode, a counter electrode lead 14 and a lead 34 of a second counter electrode are shown. Meanwhile, a measuring apparatus 81 comprises connectors 72, 96, 74 and 84 which are connected to the leads 12, 16, 14 and 34, respectively. The connector 74 and the connector 84 are connected to a current generating circuit 97. To the connector 72 is connected a potential generating circuit 82 and a current/voltage conversion circuit 78. The current/voltage conversion circuit 78, an A/D conversion circuit 79 and a CPU 80 perform the same functions as those of the measuring apparatus as described in Embodiment 1.

When the sensor 80 is set to the above-described measuring apparatus 81 and a sample containing glucose is brought in contact with a sample supply inlet 23 at the end of the sensor, the sample readily reaches the reagent layer in the sample supply pathway by capillarity. Upon the detection of arrival of the sample at the electrode system, the measuring apparatus starts operating and a timer starts measuring time. After a lapse of an appropriate time from the start of operation of the apparatus, a voltage of 300 mV is applied to a working electrode 11 with respect to the reference electrode 15 from the potential generating circuit 82, and a current oxidizing potassium ferrocyanide flows between the working electrode 11 and the counter electrode. The value of this current is displayed on an LCD 81 as the glucose concentration of the sample by the functions of the current/voltage conversion circuit 78 and other components of the measuring apparatus in the same manner as in Embodiment 1.

The sensor response value of the biosensor according to this embodiment increases in comparison with conventional biosensors for the same reasons as those of Embodiment 1. Further, owing to the provision of the reference electrode 15, the potential of the working electrode 11 is stabilized in comparison with the case without the reference electrode. Therefore, measurements with higher accuracy become possible.

As the first base plate and the second base plate of the present invention, it is possible to use any electrically insulating material having sufficient rigidity during storage and measurement. Such examples include thermoplastic resins, such as polyethylene, polystyrene, poly vinyl chloride, polyamide and saturated polyester resin, or thermosetting resins, such as urea resin, melamine resin, phenol resin, epoxy resin and unsaturated polyester resin. Among them, polyethylene terephthalate is preferable in terms of the adhesion to the electrode. As the spacer member, similar materials to those of the first and second base plates may be used. Also, the function of the spacer may be performed by the binder for bonding the first base plate and the second base plate together.

As the working electrode, it is possible to use any conductive material which is not subject to oxidation upon oxidation of the electron mediator. As the counter electrode, it is possible to use any commonly used conductive material, for example, carbon and noble metal such as palladium, gold and platinum. It is preferable that the working electrode and the counter electrode be composed mainly of noble metal among them. This enables the electrodes to be worked more finely and therefore enables higher accuracy and reduction of sample amount.

Although this embodiment employed photo lithography as a manufacturing method of the electrode system, there is no limitation thereto. For example, an electrode is produced by sputtering noble metal over a base plate to form a noble metal film and trimming it by a laser.

As the oxidoreductase, one adequate for the substrate, which is a measuring target, contained in the sample may be used. Such examples include fructose dehydrogenase, glucose oxidase, glucose dehydrogenase, alcohol oxidase, lactate oxidase, cholesterol oxidase, xanthine oxidase, amino acid oxidase, etc.

The reagent layer may contain a hydrophilic polymer. Various hydrophilic polymers may be used. Such examples include hydroxyethyl cellulose, hydroxypropyl cellulose, methyl cellulose, ethyl cellulose, ethylhydroxyethyl cellulose, carboxymethyl cellulose, polyvinyl pyrrolidone, polyvinyl alcohol, polyamino acid such as polylysine, polystyrene sulfonate, gelatin and its derivatives, polyacrylic acid and its salts, polymethacrylic acid and its salts, starch and its derivatives, and a polymer of maleic anhydride or its salt. Among them, carboxymethyl cellulose, hydroxyethyl cellulose and hydroxypropyl cellulose are preferred.

In the following, the present invention will be described more specifically with reference to examples.

EXAMPLE 1

A glucose sensor having the structure as illustrated in Embodiment 1 was produced. In this example, each of the working electrode 11 and the first counter electrode 13 was a comb-shaped electrode having 65 branches at intervals of 15 μm, each branch being 5 μm in width, and the working electrode branches and the counter electrode branches were arranged alternately at intervals of 5 μm.

The reagent layer was formed by dropping an aqueous solution containing GOD and potassium ferricyanide onto the electrode system of the first base plate 1 and drying it. Further, a surfactant layer containing lecithin as a surfactant was formed on the reagent layer.

Thereafter, using solutions containing certain amounts of glucose as samples, glucose concentrations were measured. In this example, the first counter electrode 13 and the second counter electrode 33 were short-circuited to make them function as a counter electrode. A sample was supplied to the sample supply pathway from the sample supply inlet 23. 25 seconds after the supply of the sample, a voltage of 300 mV was applied to the working electrode 11 with respect to the counter electrode. 5 seconds after the voltage application, the value of the current flowing between the working electrode 11 and the counter electrode was measured, and the measured current value was converted into a voltage value by the current/voltage conversion circuit 78. This voltage value serves as an index of the magnitude of the current flowing between the electrodes. As a result, the current response observed was proportional to the glucose concentration of the sample.

As a comparative example, response measurements were performed similarly on a sensor whose counter electrode was the first counter electrode 13 only. In this case, the switch 75 was closed, but the switch 76 remained open.

As a result, for both of the sensors of Example 1 and the comparative example, the current response observed was proportional to the glucose concentration of the sample. However, the biosensor of Example 1 yielded higher response values than the biosensor of the comparative example. This high sensitivity is probably because in Example 1, due to the presence of the second counter electrode, the reduced form electron mediator which has diffused in a direction perpendicular to the working electrode is also oxidized on the second counter electrode, and because due to the suppression of growth of the diffusion layer on the working electrode, the concentration of the oxidation/reduction species on the second counter electrode is reflected in the sensor response, or for other reasons.

EXAMPLE 2

A glucose sensor having the structure as illustrated in Embodiment 2 was produced. In this example, each of the first working electrode 41 and the second counter electrode 63 was a comb-shaped electrode having 32 branches at intervals of 15 µm, each branch being 5 µm in width, and each of the second working electrode 61 and the first counter electrode 43 was a comb-shaped electrode having 33 branches at intervals of 15 µm, each branch being 5 µm in width. The first working electrode branches and the first counter electrode branches were arranged alternately at intervals of 5 µm, and the second working electrode branches and the second counter electrode branches were arranged alternately at intervals of 5 µm. Then, the sensor was fabricated such that the first working electrode was opposed to the second counter electrode and the second working electrode was opposed to the first counter electrode. The reagent layer and the surfactant layer have the same structure as in Example 1.

In the same manner as in Example 1, using solutions containing certain amounts of glucose as samples, glucose concentrations were measured. In this example, the first counter electrode 43 and the second counter electrode 63 were short-circuited to make them function as a counter electrode, and the first working electrode 41 and the second working electrode 61 were short-circuited to make them function as a working electrode. A sample was supplied to the sample supply pathway from the sample supply inlet 52, and 25 seconds later, a voltage of 300 mV was applied to the working electrode with respect to the counter electrode. As a result, the response value obtained was higher in comparison with the sensor of the comparative example used in Example 1.

EXAMPLE 3

A sensor which was the same as that of Example 1 except for the addition of the reference electrode 15 as illustrated in FIG. 6 was produced. The sensor was set to a measuring apparatus as illustrated in FIG. 9, and a sample was supplied to the sample supply pathway from the sample supply inlet 23. 25 seconds after the supply of the sample, a voltage of 300 mV was applied to the working electrode 11 with respect to the reference electrode 15. 5 seconds after the voltage application, the value of the current flowing between the working electrode 11 and the counter electrode was measured, and the measured current value was converted into a voltage value by the current/voltage conversion circuit 78.

The sensor of Example 3 yielded highly sensitive response similarly to the sensor of Example 1. Further, since it had the reference electrode, the potential of the working electrode could be stabilized in comparison with the two-electrode system and the variation in response value was therefore reduced.

In the foregoing examples, the width of each branch of the working electrode and the counter electrode was 10 µm and the distance between the working electrode and the counter electrode on the same base plate was 5 µm, but there is no limitation thereto. Also, the time from the supply of the sample until the voltage application was 25 seconds, but there is no limitation thereto. The time may be any time during which enzyme reactions proceed to such an extent that it becomes possible to obtain current response correlated with the substrate concentration of the sample and may be preferably 180 seconds or less.

The voltage applied to the electrode system was 300 mV, but there is no limitation thereto. It may be any voltage at which the electrode reaction of the electron mediator proceeds on the working electrode.

With respect to the distance between the working electrode and the counter electrode, the distance between the working electrode branch and the counter electrode branch formed on the same base plate is preferably in a range of 1 to 50 µm. The distance between the electrode of the first base plate and the electrode of the second base plate is defined by the thickness of the spacer. The thickness of the spacer is preferably in a range of 1 to 50 µm.

Although potassium ferricyanide was used as the electron mediator in the examples, there is no limitation thereto, and p-benzoquinone, phenazine methosulfate, methylene blue, ferrocene derivatives and the like may also be used. Also, when oxygen is used as the electron mediator, current response is obtained. As the electron mediator, two or more of these may be used.

Although the first counter electrode and the second counter electrode were short-circuited to serve as the counter electrode in the foregoing examples, there is no limitation thereto, and the first counter electrode and the second counter electrode may be caused to function independently.

For example, a constant potential capable of reducing the electron mediator may be applied to the first counter electrode, and only the second counter electrode may be used as the counter electrode.

Although the aqueous solution of β-D-glucose was used as a sample in the foregoing examples, there is no limitation thereto. For example, biological samples such as whole blood, plasma, serum, interstitial fluid, saliva and urine may be used. Examples of the whole blood sample include capillary blood which is taken by puncturing the skin of a finger or an arm, venous blood and arterial blood.

Industrial Applicability

As described above, according to the present invention, it is possible to obtain a highly sensitive biosensor capable of yielding good response even when the amount of a sample is extremely small.

The invention claimed is:

1. A biosensor including: a first insulating base plate which has a first working electrode comprising a plurality of branches and a first counter electrode comprising a plurality of branches, said branches of the first working electrode and the first counter electrode being arranged alternately; a second insulating base plate which has a second working electrode comprising a plurality of branches and a second counter electrode comprising a plurality of branches, said branches of the second working electrode and the second counter electrode being arranged alternately; a reagent system comprising an oxidoreductase; and a sample supply pathway formed between the first and second insulating base plates, wherein said branches of the first working electrode and the first counter electrode that are arranged alternately, said branches of the second working electrode and the second counter electrode that are arranged alternately, and the reagent system are exposed in said sample supply pathway.

2. The biosensor in accordance with claim 1, wherein the second counter electrode is disposed at a position opposite to the first working electrode, and the second working electrode is disposed at a position opposite to the first counter electrode.

3. A method for measuring a substrate in a sample, using a biosensor including: a first insulating base plate which has a working electrode comprising a plurality of branches and a first counter electrode comprising a plurality of branches, said branches of the working electrode and the first counter electrode being arranged alternately; a second insulating base plate which has a second counter electrode and which is disposed at a position opposite to the first insulating base plate; a reagent system comprising an oxidoreductase and an electron mediator; and a sample supply pathway formed between the first and second insulating base plates, wherein said branches of the working electrode and the first counter electrode that are arranged alternately, the second counter electrode, and the reagent system are exposed in said sample supply pathway, said method comprising the steps of:

supplying a sample to said sample supply pathway;

applying a voltage between the working electrode and the first and second counter electrodes so that the working electrode oxidizes a reduced form of the electron mediator and the first and second counter electrodes function to reduce an oxidized form of the electron mediator; and measuring a current flowing between the working electrode and the first and second counter electrodes.

4. The method for measuring a substrate in a sample in accordance with claim 3, wherein the second counter electrode is disposed only at a position opposite to the working electrode in said sample supply pathway.

* * * * *